US00PP31079P2

(12) United States Plant Patent
Bacon

(10) Patent No.: US PP31,079 P2
(45) Date of Patent: Nov. 19, 2019

(54) PLUM TREE NAMED 'SUPLUMFIFTYFIVE'

(50) Latin Name: *Prunus salicina*
Varietal Denomination: Suplumfiftyfive

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 16/350,358

(22) Filed: Nov. 6, 2018

(51) Int. Cl.
*A01H 5/08* (2018.01)
*A01H 6/74* (2018.01)

(52) U.S. Cl.
USPC ..... Plt./184

(58) Field of Classification Search
USPC ..... Plt./180, 184
See application file for complete search history.

*Primary Examiner* — Susan McCormick Ewoldt
(74) *Attorney, Agent, or Firm* — Knobbe, Martens, Olson & Bear, LLP

(57) ABSTRACT

A new and distinct plum tree variety, *Prunus salicina*, cv. 'Suplumfiftyfive' is characterized by having early-ripening fruit that is large, with black skin and red flesh. The fruit of the new variety 'Suplumfiftyfive' also has firm flesh, a sweet-mild flavor and a stone that is semi-free from the flesh. The date of ripening of the fruit of the new variety is approximately June 10.

1 Drawing Sheet

Latin name of the genus and species claimed: *Prunus salicina.*

Variety denomination: 'Suplumfiftyfive'.

BACKGROUND AND SUMMARY OF THE INVENTION

This application relates to the discovery and asexual propagation of a new and distinct variety of plum tree, *Prunus salicina* cv. 'Suplumfiftyfive'. The new variety was first originated by hybridization in September 2011 by Terry A. Bacon as breeder number 'PL1347RB'.

The new variety 'Suplumfiftyfive' is characterized by having early-ripening fruit that is large, with black skin and red flesh. The fruit of the new variety 'Suplumfiftyfive' also has firm flesh, a sweet-mild flavor and a stone that is semi-free from the flesh.

The seed parent is 'PL671RB' (unpatented breeding selection), and the pollen parent is 'Suplumfortyone' (U.S. Plant Pat. No. 22,430). The parent varieties were first crossed in February 2009, with the date of first sowing being February 2010, and the date of first flowering being February 2011. The new plum variety 'Suplumfiftyfive' was first asexually propagated by Terry Bacon near Wasco, Kern County, Calif. in February 2013 by dormant grafting.

The new variety 'Suplumfiftyfive' resembles its pollen parent 'Suplumfortyone' in that both have fruit with red flesh, but the fruit of the new variety 'Suplumfiftyfive' is larger at 128 g compared to 117 g for 'Suplumfortyone'. The fruit of new variety 'Suplumfiftyfive' begins ripening about June 10th about 18 days later than for 'Suplumfortyone'.

The new variety 'Suplumfiftyfive' resembles its seed parent 'PL671RB' in that both have fruit with red flesh, but the fruit of the new variety 'Suplumfiftyfive' is larger at 128 g compared to 69 g for 'PL671RB'. The fruit of new variety 'Suplumfiftyfive' begins ripening about 12 days earlier than for 'PL671RB'.

The fruit of the new variety 'Suplumfiftyfive' ripens at about the same time as the fruit of 'Black Splendor' (unpatented), and both varieties have fruit with red flesh. The new variety 'Suplumfiftyfive' has a brix of 17% and the Brix:Acid is 36 compared to a brix of 14% and a Brix:Acid of 25 for 'Black Splendor'. The flesh of the fruit of the new variety 'Suplumfiftyfive' resembles the red flesh of 'Flavorosa' (U.S. Plant Pat. No. 10,285), but the new variety begins ripening about 15 days earlier than 'Flavorosa'.

The new variety 'Suplumfiftyfive' also differs from 'Flavorosa' in the fruit size. In particular, the fruit of the new variety is 63 mm compared to 56 mm for 'Flavorosa'.

The new variety 'Suplumfiftyfive' has been shown to maintain its distinguishing characteristics through successive asexual propagations by, for example, cuttings and grafting.

BRIEF DESCRIPTION OF THE PHOTOGRAPH

The accompanying color photographic illustration FIG. 1 shows typical specimens of the foliage and fruit of the present new plum variety 'Suplumfiftyfive'. The illustration shows the upper and lower surface of the leaves, a view of the fruit as a whole, the stone as a whole, and a sectional view of a fruit divided across its suture plane to show flesh color, pit cavity and the stone remaining in place. The photographic illustration was taken shortly after being picked and the colors are as nearly true as is reasonably possible in a color representation of this type. The photographs depict fruit and vegetative growth from a six year old tree.

DETAILED DESCRIPTION

Throughout this specification, color names beginning with a small letter signify that the name of that color as used in common speech is aptly descriptive. Color names beginning with a capital letter designate values based upon The R.H.S. Colour Chart published by The Royal Horticultural Society, London, England, 1986.

The descriptive matter which follows pertains to six-year-old 'Suplumfiftyfive' plants grown in the vicinity of Wasco, Kern County, Calif. during 2018 and is believed to apply to plants of the variety grown under similar conditions of soil and climate elsewhere.

TREE

General: (Measurements taken on six year old trees unless otherwise noted).

*Size*.—Medium, reaches a height of approximately 3 meters with normal pruning.

*Habit*.—Upright-spreading.

*Vigor*.—Medium, top shoot growth of at 1 meter during the growing season.

*Productivity*.—Very productive.

*Bearer*.—On spurs and long shoots.

*Fertility*.—Self-incompatible; requires pollinator.

*Hardiness*.—Hardy in all fruit growing areas of California. Winter chilling requirement is approximately 300 hours at or below 7.2° C.

*Disease resistance/susceptibility*.—No specific testing for relative plant disease resistance/susceptibility has been conducted. Under close observation in Kern County, Calif., no particular plant/fruit disease resistance/susceptibility has been observed.

*Insect resistance/susceptibility*.—No specific testing for relative plant disease resistance/susceptibility has been conducted. Under close observation in Kern County, Calif., no particular plant/fruit insect resistance/susceptibility has been observed.

Trunk: (Measurements at approximately 30 cm above soil line on mature tree).

*Diameter*.—Approximately 14 cm.

*Texture*.—Medium shaggy, increasing with age of tree.

*Trunk color*.—About Medium Greyed-Green 198B with highlights of Medium Greyed-Orange 166C, becoming darker with age.

Branches: (Measurements at approximately 90 cm above soil line).

*Size*.—Diameter approximately 7 cm.

*Texture*.—Medium shaggy, increasing with age.

*Color*.—About Dark Grey 201B with highlights of about Medium Grey-Brown 199B, becoming darker with age.

*Lenticels*.—Present.

*Lenticels density*.—Plentiful, about 12/cm$^2$.

*Lenticels color*.—About Light Grey 201D.

*Lenticels dimensions*.—Length: approximately 3 mm. Width: approximately 1 mm.

One year old shoots: (Data taken in September at mid-point of current season growth).

*Size*.—Average diameter approximately 6 mm.

*Color*.—Topside: About Dark Greyed-Orange 177A. Underside: About Dark Greyed-Orange 177A.

*Lenticels*.—Plentiful.

*Lenticels diameter*.—Approximately 0.5 mm.

*Lenticels color*.—About Light Grey 201D.

*Internode length*.—Approximately 2 cm. Midway on shoot.

*Spur length*.—Medium, usually 10 mm.

*Anthocyanin intensity on upper side of shoot*.—Strong.

Vegetative buds:

*Position of vegetative bud in relation to shoot*.—Slightly held out.

*Size*.—Medium, approximately 1.5 mm×2.5 mm.

*Shape*.—Conical.

*Bud shape at apex*.—Acute.

*Color*.—About Dark Greyed-Orange 177A.

Flower buds:

*Shape*.—Acute.

*Dimensions*.—Approximately 1.5 mm×2.8 mm.

*Color*.—About Dark Greyed-Orange 177A.

*Distribution*.—2-6 buds, generally on spurs and one year old shoots.

*Ratio of flowering buds to vegetative buds*.—2-6 flower buds to 1 vegetative bud.

FOLIAGE

Leaves: (Data taken in June on fully expanded leaves at mid-point of the current season growth).

*Average length*.—Medium; approximately 85 mm without petiole.

*Average width*.—Approximately 40 mm.

*Length/width ratio*.—Moderately elongated, about 2:1.

*Color*.—Upper surface: About Dark Green 136A. Lower surface: About Medium Green 139B.

*Glossiness of upper side*.—Medium.

*Angle at apex* (*excluding tip*).—Right angled.

*Base*.—Acuminate.

*Vein color*.—About Medium Yellow-Green 145A.

*Venation*.—Pinnately net veined.

*Surface texture*.—Smooth on both upper and lower surfaces.

*Shape in the cross section*.—Concave.

*Profile*.—Up folded.

*Leaf blade tip*.—Curved downwardly.

*Undulation of margin*.—Slight.

*Density of pubescence of lower side*.—Absent or very sparse.

*Incisions of margin*.—Bi-crenate.

Petiole:

*Average length*.—Approximately 12 mm.

*Average diameter*.—Approximately 2 mm.

*Color*.—About Medium Green 133B with highlights of Medium Greyed-Orange 176C where exposed to sun.

Stipules:

*Number/leaf bud*.—Usually one.

*Typical length*.—Approximately 8 mm.

*Color*.—About Dark Greyed-Orange 166A when dried.

*Persistence*.—Falls off.

Leaf glands:

*Average number and arrangement*.—0-2, predominately on the petiole at base of leaf blades.

*Form*.—Globose.

*Diameter*.—Approximately 0.5 mm.

*Color*.—About Medium Greyed-Yellow 162A becoming Dark Greyed-Orange 166A over time.

FLOWERS

General:

*Time of beginning of flowering*.—Very early for the San Joaquin Valley, Calif.

*Flower blooming period*.—First bloom: Approximately February 10 in Wasco, Calif. Full bloom: Approximately February 14 in Wasco, Calif.
*Location of first bloom*.—Tips of one year old shoots.
*Location of full bloom*.—Central part of the tree canopy.
*Duration of bloom*.—Approximately 10 days.
*Flower diameter*.—Medium, approximately 20 mm.
*Flower form*.—Showy.

Pedicels:
*Length*.—Medium, approximately 10 mm.
*Diameter*.—Approximately 1.2 mm.
*Color*.—About Light Green 139D.
*Pubescence*.—Absent.

Petals:
*Number*.—5.
*Arrangement*.—Overlapping.
*Color*.—About White 155A.
*Length*.—Medium, approximately 8 mm.
*Width*.—Approximately 7 mm.
*Shape*.—Circular.
*Apex shape*.—Rounded.
*Base shape*.—Narrows at point of attachment.
*Surface texture*.—Smooth.
*Undulation of margins*.—Medium.
*Frequency of flowers with double petals*.—None.
*Claw*.—Absent.

Sepals:
*Number*.—5.
*Length*.—Approximately 4 mm.
*Diameter*.—Approximately 3 mm.
*Shape*.—Medium ovate.
*Color*.—About Light Green 139D.
*Surface texture*.—Smooth.
*Margins*.—Undulating.
*Positioning*.—Adpressed to petals.
*Frequency of flowers with double sepals*.—None.

Stamens:
*Number*.—Approximately 25-32, usually 28.
*Average length*.—Variable, ranging from 3 mm to 10 mm.
*Filament color*.—About White 155A.
*Flower pollen color*.—About Light Yellow-Orange 18C.
*Position*.—Perigynous.

Pistil:
*Average length*.—Approximately 3-4 mm.
*Ovary diameter*.—Approximately 2 mm.
*Pubescence*.—Absent.
*Stigma extension in comparison to anthers*.—Usually above.
*Style frequency of supplementary pistils*.—Few.

Receptacle:
*Depth*.—Medium, approximately 4 mm.
*Pubescence of inner surface*.—Absent.
*Pubescence of outer surface*.—Absent.

FRUIT

General: (Description taken at firm-mature near Wasco, Kern County, Calif.).

Ripening:
*Time of beginning of fruit ripening*.—Early.
*Date of first pick*.—Approximately June 10.
*Date of last pick*.—Approximately June 20.

Size:
*Height*.—Tall, approximately 65 mm.
*Diameter in line with suture plane*.—Approximately 63 mm.
*Diameter perpendicular to suture plane*.—Broad, approximately 63 mm.
*Average weight*.—Large, approximately 128 gm.

Peduncle:
*Length of stem*.—Short, approximately 7 mm.
*Diameter of stem*.—Approximately 3 mm.
*Color of sent*.—About Light Green 139D.

Shape:
*Viewed from apex*.—Circular.
*Viewed in-line with suture*.—Circular.
*Viewed from side, perpendicular to suture*.—Circular.
*Symmetry*.—Symmetric.
*Shape of base*.—Truncate.
*Shape of apex*.—Depressed.

Fruit stem cavity:
*Depth of stalk cavity*.—Shallow; Approximately 5 mm.
*Width of stalk cavity*.—Medium; Approximately 15 mm.
*Depth of suture*.—Absent or very shallow.

Fruit skin:
*Thickness*.—Medium, typical of most varieties.
*Flavor*.—Mildly-tart.
*Adherence to flesh*.—Strong.
*Surface texture*.—Smooth.
*Pubescence*.—None.
*Bloom*.—Medium.
*Ground color*.—Not visible.
*Overcolor*.—About Dark Greyed-Purple 187A, becoming fully Dark Black 202A.
*Relative area of overcolor*.—Whole surface.
*Pattern of overcolor*.—Solid.
*Reticulation*.—Absent.
*Tendency to crack*.—Rare.
*Number of lenticels*.—Many.
*Size of lenticels*.—Medium, approximately 0.5 mm to 1 mm.

Flesh:
*Ripens*.—Evenly.
*Texture*.—Firm-juicy.
*Flavor*.—Sweet-mild.
*Color*.—About Dark Red 53A.
*Firmness*.—Firm, typically 10 lb to 13 lb pressure at harvest.
*Juice*.—High, able to squeeze free juice easily.
*Acidity*.—Medium, 0.47% titratable acidity.
*Sweetness*.—High, about 17% Brix at harvest.
*Adherence to stone*.—Semi-free.
*Amount of fiber*.—Low.

Fruit use: Fresh market.

Fruit shipping and keeping quality: Good.

Stone:
*Stone freeness*.—Semi-free.
*Stone size*.—Size: Medium. Length: Approximately 20 mm. Diameter in line with suture plan: Approximately 19 mm. Diameter perpendicular to suture plane: Approximately 9 mm.
*Color*.—About Medium Greyed-Yellow 161B when dried.
*Position of maximum diameter*.—Middle.
*Shape from lateral view*.—Circular.
*Shape from ventral view*.—Medium elliptic.

*Shape from basal view*.—Medium elliptic.
*Base shape*.—Nearly straight.
*Apex shape*.—Pointed.
*Stone ridges*.—Rounded throughout.
*Stone outgrowing keel*.—Well developed.
*Ventrical edge*.—Thin with wing toward middle.
*Dorsal edge*.—Narrow, shallow grooves throughout.
*Fibers*.—Not visible.
*Symmetry in lateral view*.—Moderately asymmetrical.
*Texture of lateral surface*.—Rough.
*Width of stalk-end*.—Medium.
*Tendency to split*.—Rare.

What is claimed is:

1. A new and distinct variety of plum tree as herein described and illustrated.

* * * * *

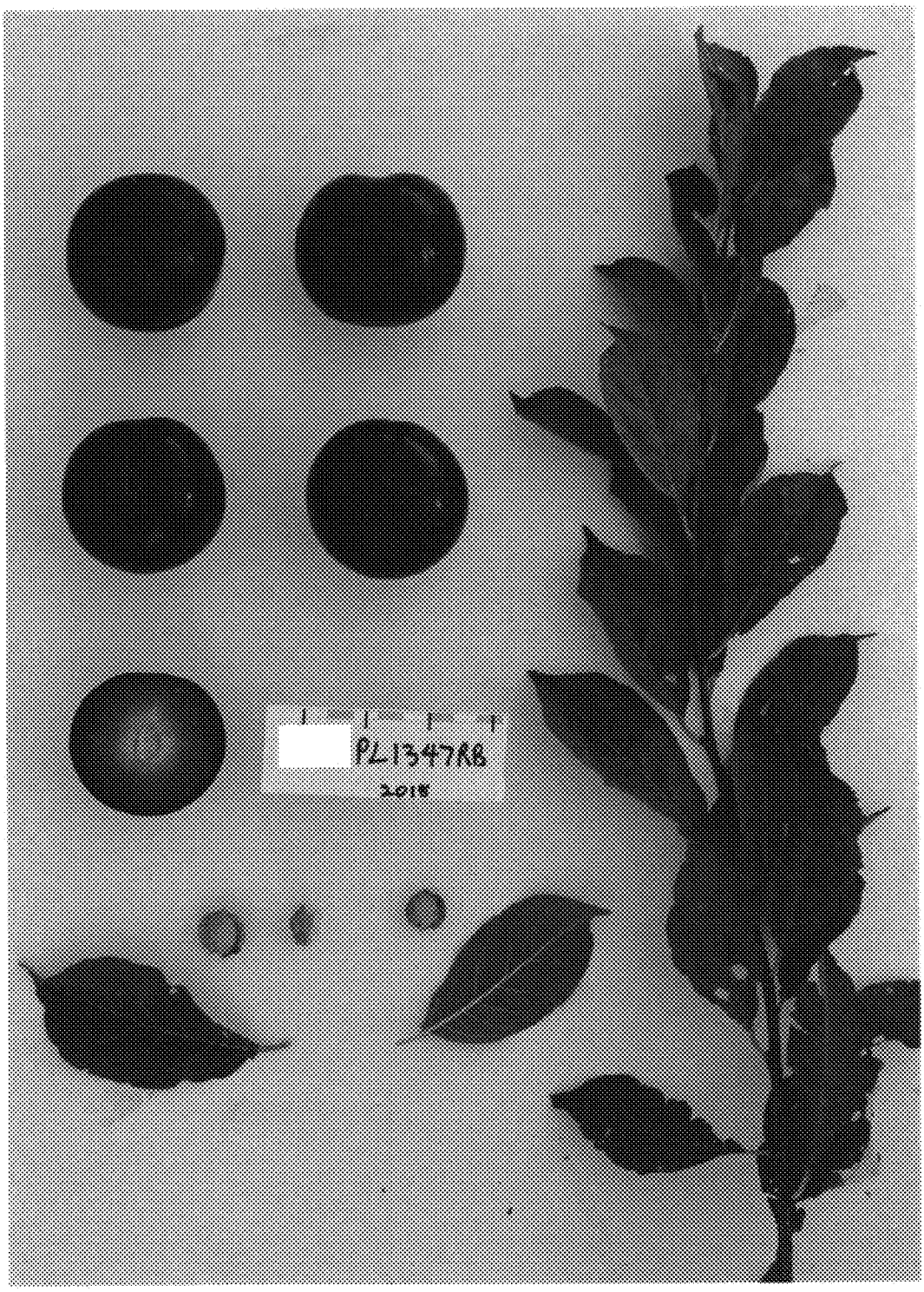
PL1347RB
2018